US008221329B2

(12) United States Patent
Hartings et al.

(10) Patent No.: US 8,221,329 B2
(45) Date of Patent: Jul. 17, 2012

(54) INHALATION SYSTEM AND METHOD

(75) Inventors: Justin M. Hartings, Clarksburg, MD (US); Chad J. Roy, Keedysville, MD (US); Gerald M. Liverette, Germantown, MD (US)

(73) Assignee: The United State of America as represented by the Secretary of the Army, Washington, DC (US)

( * ) Notice: Subject to any disclaimer, the term of this patent is extended or adjusted under 35 U.S.C. 154(b) by 152 days.

(21) Appl. No.: 10/364,855

(22) Filed: Feb. 10, 2003

(65) Prior Publication Data

US 2003/0125633 A1 Jul. 3, 2003

Related U.S. Application Data

(63) Continuation-in-part of application No. 10/166,228, filed on May 29, 2002, now Pat. No. 7,377,276, and a continuation-in-part of application No. 09/919,741, filed on Jul. 31, 2001, now Pat. No. 6,904,912.

(60) Provisional application No. 60/396,698, filed on Jul. 17, 2002.

(51) Int. Cl.
*A61B 5/08* (2006.01)
(52) U.S. Cl. .................. 600/535; 600/300; 600/529
(58) Field of Classification Search .................. 600/532, 600/300; 73/23.3; 422/84; 128/204.23
See application file for complete search history.

(56) References Cited

U.S. PATENT DOCUMENTS

| | | | |
|---|---|---|---|
| 3,230,577 A | 1/1966 | Hughes | |
| 3,548,840 A | 12/1970 | Baumgartner | |
| 3,944,387 A * | 3/1976 | Schreckendgust | 422/3 |
| 4,053,604 A | 10/1977 | Jaramillo | |
| 4,201,154 A | 5/1980 | Gowrie | 119/15 |

(Continued)

FOREIGN PATENT DOCUMENTS

EP 0 610 171 B1 9/1994

(Continued)

OTHER PUBLICATIONS

Emka Technologies, "*Software and Hardware for Pulmonary Applications*", 1 pg.

(Continued)

*Primary Examiner* — Patricia Mallari
*Assistant Examiner* — Michael D'Angelo
(74) *Attorney, Agent, or Firm* — Elizabeth Arwine; Cahn & Samuels, LLP

(57) ABSTRACT

A system includes but is not limited to at least one manifold; an inhalant dissemination device coupled to the at least one manifold; an inhalant characterization device coupled to the at least one manifold; and a control module operably coupled to the inhalant dissemination device and the inhalant characterization device, said control module configured to (a) determine an inhalant concentration in a manifold, and (b) calculate at least one of a retrospective and a prospective inhaled dose in response to the inhalant concentration, and (c) start and stop a flow through the manifold until the at least one of the retrospective and the prospective inhaled dose is greater than or equal to a specified dose. A method includes but is not limited to starting a flow of an inhalant through a manifold; determining an inhalant concentration of the inhalant in the manifold; and stopping the flow of the inhalant through the manifold when the inhalant concentration is in a first specified inhalant-concentration range.

23 Claims, 2 Drawing Sheets

U.S. PATENT DOCUMENTS

| | | | |
|---|---|---|---|
| 4,216,741 A | 8/1980 | Moss | 119/15 |
| D262,320 S | 12/1981 | Monö | D24/62 |
| 4,305,347 A | 12/1981 | Hemenway et al. | 119/15 |
| 4,347,712 A | 9/1982 | Benton et al. | |
| 4,348,985 A | 9/1982 | Leong | 119/15 |
| 4,402,315 A | 9/1983 | Tsuda et al. | |
| 4,463,706 A | 8/1984 | Meister et al. | |
| 4,510,929 A | 4/1985 | Bordoni et al. | 128/200.14 |
| 4,520,808 A | 6/1985 | LaBauve | 128/200.14 |
| 4,532,892 A | 8/1985 | Kuzara | |
| 4,570,630 A | 2/1986 | Elliott et al. | 128/203.15 |
| 4,598,704 A | 7/1986 | Bordoni et al. | 128/200.14 |
| 4,622,976 A * | 11/1986 | Timpe et al. | 600/431 |
| 4,674,490 A | 6/1987 | Frankel et al. | 128/200.14 |
| 4,703,753 A | 11/1987 | Bordoni et al. | 128/200.14 |
| 4,710,887 A * | 12/1987 | Ho | 702/24 |
| 4,721,060 A | 1/1988 | Cannon et al. | 119/15 |
| 4,724,845 A | 2/1988 | Callahan | |
| 4,781,146 A | 11/1988 | Spengler | |
| 4,787,384 A | 11/1988 | Campbell et al. | |
| 4,811,729 A | 3/1989 | Sands et al. | |
| 4,860,741 A | 8/1989 | Bernstein et al. | 128/204.18 |
| 4,940,051 A | 7/1990 | Lankinen | 128/200.18 |
| 4,986,267 A | 1/1991 | Doss | |
| 5,025,619 A * | 6/1991 | Cannon | 119/300 |
| 5,082,471 A * | 1/1992 | Athayde et al. | 95/51 |
| 5,099,792 A | 3/1992 | Cannon et al. | 119/15 |
| 5,109,797 A | 5/1992 | Briant et al. | 119/15 |
| 5,156,776 A * | 10/1992 | Loedding et al. | 261/27 |
| 5,297,502 A | 3/1994 | Jaeger | 119/15 |
| 5,320,108 A | 6/1994 | Cloutier | |
| 5,379,777 A | 1/1995 | Lomask | 128/716 |
| 5,467,764 A * | 11/1995 | Gamow | 128/202.12 |
| 5,598,838 A | 2/1997 | Servidio et al. | |
| 5,622,164 A | 4/1997 | Kilis et al. | 128/200.24 |
| 5,626,130 A | 5/1997 | Vincent et al. | 128/203.12 |
| 5,685,293 A | 11/1997 | Watt | |
| 5,799,652 A | 9/1998 | Kotliar | |
| 5,887,586 A | 3/1999 | Dahlbäck et al. | 128/204.22 |
| 5,896,829 A * | 4/1999 | Rothenberg et al. | 119/417 |
| 5,935,516 A | 8/1999 | Baugh | |
| 5,954,049 A | 9/1999 | Foley et al. | 128/204.18 |
| 5,975,081 A | 11/1999 | Hood et al. | |
| 6,016,803 A * | 1/2000 | Volberg et al. | 128/205.26 |
| 6,054,161 A * | 4/2000 | Palmer | 426/312 |
| 6,056,885 A * | 5/2000 | Wasinger | 210/760 |
| 6,079,483 A | 6/2000 | Morooka et al. | |
| 6,131,571 A | 10/2000 | Lampotang et al. | 128/204.21 |
| 6,138,668 A | 10/2000 | Patton et al. | 128/200.14 |
| 6,192,876 B1 * | 2/2001 | Denyer et al. | 128/205.25 |
| 6,347,628 B1 | 2/2002 | Maison | |
| 6,352,076 B1 | 3/2002 | French | 119/420 |
| 6,380,859 B1 * | 4/2002 | Brownlee | 340/576 |
| 6,565,624 B2 * | 5/2003 | Kutt et al. | 95/8 |
| 6,584,971 B1 * | 7/2003 | Denyer et al. | 128/203.14 |
| 6,620,379 B1 * | 9/2003 | Piuk et al. | 422/3 |
| 6,694,977 B1 | 2/2004 | Federowicz et al. | |
| 6,725,859 B1 | 4/2004 | Rothenberg et al. | |
| 6,904,912 B2 | 6/2005 | Roy et al. | |
| 7,377,276 B2 | 5/2008 | Roy et al. | |

FOREIGN PATENT DOCUMENTS

| | | |
|---|---|---|
| EP | 0 667 168 B1 | 6/2000 |
| WO | WO 91/06832 | 5/1991 |
| WO | WO 96/13294 A1 | 5/1996 |

OTHER PUBLICATIONS

Emka Technologies, "*Develops, Manufactures and sells hardware and Software for Studies in Physiology, Pharmacology and Toxicology*", 1 pg.
TSE Technical and Scientific Equipment GmbH, "*TSE Exposys, Planning, Control and Analysis of Inhalation Experiments*", 11 pgs.
RCC Ltd. Pharmaceutical Industry, "*Inhalation Toxicology*", 2 pgs.
Huntingdon Life Sciences, "*Inhalation Toxicology, for Pharmaceutical Development and Safety*", 4 pgs.
Kenny, T.J. et al., "*Whole Body Exposure System for Administering Nitric Oxide (KINOX®) by Inhalation to Neonate Rats*," Huntingdon Life Sciences, 4 pgs.
Battelle, "*NORES® Nose-Only Rodent Inhalation Exposure System*", 2 pgs.
ITR Laboratories Canada Inc., "*Inhalation Toxicology*", 2 pgs.
TSE Technical and Scientific Equipment GmbH, "*TSE OpyoPan, for Aerosol assessment during Inhalation Studies*", 6 pgs.
TSE Technical and Scientific Equipment GmbH, "*TSE Inhalation Systems, Aerosol Generation, Process Control and Analysis*", 17 pgs.
English abstract for EP 0610171 B1.
Emka Technologies. "*Software and Hardware for Pulmonary Applications*", available prior to Mar. 31, 2002. 1 pg.
Emka Technologies. "*Develops, Manufactures and Sells Hardware and Software for Studies in Physiology, Pharmacology and Toxicology*", available prior to Mar. 31, 2002, 1 pg.
TSE Technical and Scientific Equipment GmbH, "*TSE Exposys, Planning, Control and Analysis of Inhalation Experiments*", available prior to Mar. 31, 2002, 11 pgs.
RCC Ltd., "*Inhalation Toxicology*", available prior to Mar. 31. 2002, 2 pgs.
Huntingdon Life Sciences, "*Inhalation Toxicology for Pharmaceutical Development and Chemical Safety*"; available prior to Mar. 31, 2002, 4 pgs.
Kenny, T.J. et al., *Whole Body Exposure System for Administering Nitric Oxide (KINOX®) by Inhalation to Neonate Rats*, Huntingdon Life Sciences, Mar. 2002, 4 pgs.
Battelle, "*NORES® Nose-Only Rodent Inhalation Exposure System*", available prior to Mar. 31, 2002, 2 pgs.
ITR Laboratories Canada Inc., "*Inhalation Toxicology*", available prior to Mar. 31, 2002, 2 pgs.
TSE Technical and Scientific Equipment GmbH, "*TSE OptoPan, for Aerosol Assessment During Inhalation Studies*", Feb. 2002, 6 pgs.
TSE Technical and Scientific Equipment GmbH, "*TSE Inhalation Systems, Aerosol Generation, Process Control and Analysis*", available prior to Mar. 31, 2002, 17 pgs.
English Abstract for EP 0 610 171 B1, Aug. 10, 1994.
Canada Intellectual Property Office, Office Action in Canadian Patent Application No. 2,435,764, Apr. 27, 2009.

\* cited by examiner

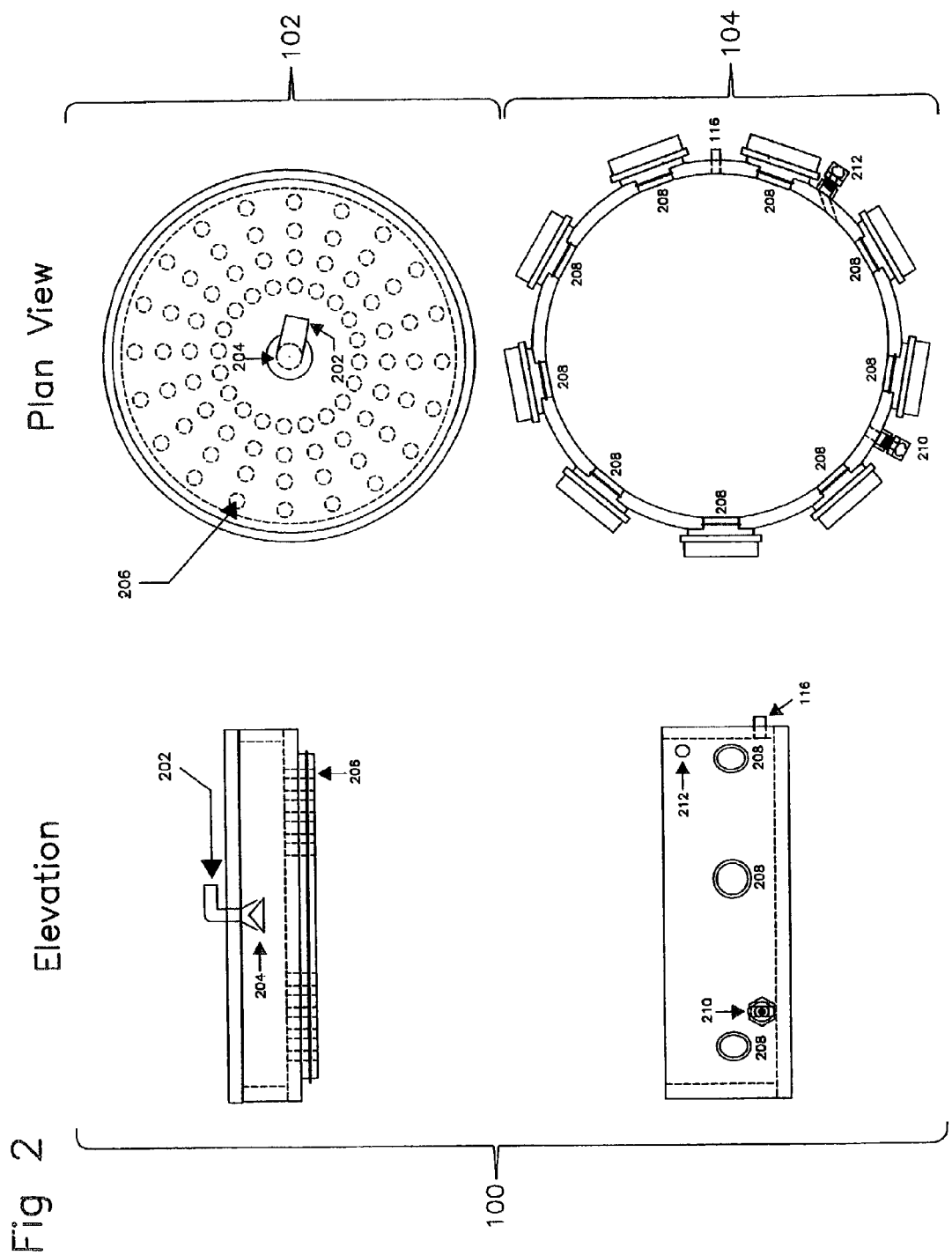

INHALATION SYSTEM AND METHOD

CROSS-REFERENCE TO RELATED APPLICATION

This application claims the benefit under 35 U.S.C. 119(e) of, and incorporates by reference in its entirety the presently U.S. Provisional Patent Application No. 60/396,698,entitled Hybrid Inhalation System for Precious Materials, filed 17 Jul. 2002,naming Justin M. Hartings, Chad J. Roy, and Gerald M. Liverette as inventors.

This application is also a continuation in part of, claims priority from, and incorporates by reference in its entirety the presently U.S. patent application Ser. No. 09/919,741, filed 31 Jul. 2001, entitled AUTOMATED INHALATION TOXICOLOGY EXPOSURE SYSTEM, now U.S. Pat. No. 6,904,912 B2, issued on 14 Jun. 2005, naming Justin M. Hartings, and Chad J. Roy as inventors.

This application is also a continuation in part of, claims priority from, and incorporates by reference in its entirety the presently U.S. patent application Ser. No. 10/166,228, filed 29 May 2002, now U.S. Pat. No. 7,377,276, entitled INHALANT SYSTEM, naming Justin M. Hartings, and Chad J. Roy as inventors.

This application also incorporates by reference in their entireties any and all applications and/or other materials which were incorporated by reference in any of the foregoing-referenced applications or any of their parent, great-grandparent, great-great grandparent, etc., applications, such as the United States Provisional Patent Application(s) incorporated therein.

STATEMENT REGARDING FEDERALLY SPONSORED RESEARCH OR DEVELOPMENT

This invention was made with support from the United States Army. The United States Army has certain rights in this invention.

BACKGROUND OF THE INVENTION

1. Field of the Invention

The subject matter disclosed herein relates, in general, to inhalation systems.

2. Description of the Related Art

Inhalation exposure chambers are designed to expose all or part of an animal to a test atmosphere. Inhalation exposure chambers have historically been conducted with either static or dynamic inhalation systems. Each of these types of systems has drawbacks.

Related-art dynamic inhalation systems operate by supplying and exhausting air from an exposure chamber at a constant rate, and necessitate continuous introduction of an inhalant into the input air stream. The inventors have recognized, and such recognition forms a part of the inventive content herein, that related-art dynamic inhalation systems entail a number of drawbacks. For example, in related-art dynamic inhalation systems the constant supply and exhaust of inhalant from the chamber results in low efficiency of inhalant delivery. Specifically, consider exposing 10 rodents, each with a respiratory minute volume of 20 ml, in a dynamic chamber running at 20 liters per minute. During a minute of exposure, the rodents respire 200 ml of air from the inhalant chamber, and 20 liters of air exit through the inhalant chamber exhaust. Thus, there would be a 1:100 ratio of respired inhalant to exhausted inhalant. This results in a wasting of over 99% of the test material during the exposure. Insofar as that most materials in pre-clinical trials or initial stages of animal testing are expensive to produce, and generally synthesized in small lots, the poor efficiency of related-art dynamic exposure systems imposes a heavy financial burden on organizations. It is therefore apparent that a need exists in the art for a method and system that will reduce the amount of test material wasted, but without sacrificing accuracy of dose.

As another example of the drawbacks of related-art dynamic inhalation systems, consider that if a user were attempting to determine the toxicity or infectiousness of a highly pathogenic aerosol, a large amount of the test material would be expended in an attempt to achieve a dose to reach the desired outcome using a related-art dynamic system. Accordingly, the amount of pathogen that needs to be aerosolized would be increased, thus potentially raising the safety risks to users of the system. It is therefore apparent that a need exists in the art for a method and system that can effectively deliver a high dose of pathogen, while substantially reducing the amount of pathogen that needs to be aerosolized in related-art dynamic inhalant systems.

As another example of the drawbacks of dynamic inhalation systems, dynamic inhalation systems are unattractive for testing so-called "aged" aerosols. In many inhalation studies the material under testing must have a long residence time in the aerosol phase to achieve the conditions needed for effective testing. Long residence times can be required, for example, to assure adequate aerosol particle drying or to allow aerosol mediated chemical reactions to occur before inhalation. Because of the high throughput of related-art dynamic inhalation systems, such systems often do not provide the longer inhalant residence times needed for these studies. For example, related-art dynamic systems have aerosol residence times of less than a minute. A system that could increase these times would be advantageous for inhalation studies requiring aged aerosols.

Related-art static inhalation systems operate by disseminating an inhalant into an exposure chamber and then stopping the inhalant dissemination device and all air flows. The animals in the exposure chamber then inhale this static inhalant atmosphere. Related-art static inhalation systems have a number of drawbacks that make them unattractive for inhalation toxicology studies.

One drawback of related-art static inhalation systems is that related-art static inhalation systems do not provide a mechanism for real-time dose calculation. Related-art static inhalation systems require that the cycle time and the cycle dose be determined prior to exposure. There are no related-art static inhalation systems that allow the inhaled dose to be determined in near real-time during the exposure.

Another drawback of related-art static inhalation systems is that related-art static inhalation systems require that doses be delivered to animals in discrete units. Animals inhale the inhalant atmosphere until the inhalant concentration approaches zero. If an additional dose is required, the test atmosphere must be reestablished with the inhalant dissemination device and the animals allowed to inhale the environment until the inhalant concentration approaches zero again. When running an inhalation study with a static system, therefore, the operator must first calculate the starting concentration required for a particular number of exposure cycles to achieve a desired dose. To expose another set of animals to a different dose, the operator must recalculate the starting concentration and the number of cycles required. Static systems do not provide a mechanism for delivering any dose to the test subject with the same starting concentration and independent of the number of static cycles. The need to change inhalant starting solutions in the inhalant dissemination device results in a wasting of expensive testing materials that may be difficult to produce.

Another drawback of static inhalation systems is that static systems do not have mechanisms for automatically controlling the concentration of the inhalant in the exposure chamber. In related-art static systems, the operator must manually initiate and terminate inhalant generation. The operator then typically cycles the aerosol generator manually either at predetermined time intervals, or in response to aerosol concentration measurements. Thus, these systems are user intensive and do not produce results with the precision and accuracy allowed by computer control.

Another drawback of related-art static inhalation systems is that static inhalation systems require complete recharacterization if the number or respiratory minute volumes of animals in the system changes. Changing the number of animals or changing to a species with a different respiratory minute volume will change both the time required for the chamber concentration to approach zero and the dose delivered to the animals in each cycle. Since both the cycle time and the cycle dose vary with the number and type of animals to be exposed, related-art systems must be completely recharacterized for each change in test subjects.

Another drawback of related-art static inhalation systems is that related-art static inhalation systems result in environments rich in carbon dioxide and ammonia near the end of each exposure cycle. As the test subjects respire in the static chamber, they remove oxygen and load the environment with carbon dioxide. Waste from the subjects also results in the production of ammonia within static exposure chambers. Near the end of exposure cycles, this carbon dioxide rich environment results in exposure of the test subjects to a hypoxic and ammonia-laden atmosphere. The irritant effects of ammonia in the respiratory system paired with potential hypoxemia may interfere with the desired biological outcome from the inhalation of the material under testing, thus complicating the ability of the user to discern the biological outcome induced by the test material from the effects induced by the inhalation of the aforementioned contaminants.

BRIEF SUMMARY OF THE INVENTION

In one embodiment, a method includes but is not limited to: starting a flow of an inhalant through a manifold; determining an inhalant concentration of the inhalant in the manifold; and stopping the flow of the inhalant through the manifold when the inhalant concentration is in a first specified inhalant-concentration range. In another method embodiment, the first specified inhalant-concentration range is characterized by: an inhalant concentration greater than or equal to a specified threshold concentration. In another method embodiment, the method further includes but is not limited to: repeating said starting, determining, and stopping when the inhalant concentration is in a second specified inhalant-concentration range. In another method embodiment, the second specified inhalant-concentration range is characterized by: an inhalant concentration less than or equal to a specified threshold concentration. In another method embodiment, the method further includes but is not limited to: determining a metabolic waste product concentration in the manifold; and repeating said starting, determining, and stopping when the metabolic waste product concentration is in a first specified range. In another method embodiment, the metabolic waste product concentration is characterized by: a biological waste product concentration greater than or equal to a specified threshold concentration. In another method embodiment, the metabolic waste product is characterized by: at least one metabolic waste product of the metabolic-waste product group including but not limited to carbon dioxide and ammonia. In another method embodiment, stopping the flow of the inhalant through the manifold when the inhalant concentration is in a first specified inhalant-concentration range is characterized by: reducing an input flow down to substantially only that necessary to operate an inhalant characterization device. In another method embodiment, stopping the flow of the inhalant through the manifold when the inhalant concentration is in a first specified inhalant-concentration range is characterized by: substantially stopping an exhaust flow.

In one embodiment, a method includes but is not limited to: determining an inhalant concentration in a manifold; calculating at least one of a retrospective and a prospective inhaled dose in response to the inhalant concentration; and starting and stopping a flow through the manifold until the at least one of the retrospective and the prospective inhaled dose is greater than or equal to a specified dose. In another method embodiment, determining an inhalant concentration in a manifold is characterized by: sensing the inhalant concentration. In another method embodiment, calculating a retrospective inhaled dose in response to the inhalant concentration is characterized by: measuring an elapsed time of exposure of an animal in an animal port; determining a respiratory minute volume of the animal in the animal port; and calculating an actual inhalation dosage in response to one or more of the elapsed time, the respiratory minute volume, and the inhalant concentration. In another method embodiment, calculating a prospective inhaled dose in response to the inhalant concentration is characterized by: recalling at least one volume of an intake manifold and an exposure manifold; determining a respiratory minute volume of the animal in the animal port; and calculating a projected inhalation dosage in response to one or more of the at least one volume, the respiratory minute volume, and the inhalant concentration. In another method embodiment, recalling at least one volume of an intake manifold and an exposure manifold is characterized by: recalling at least fifteen volumes of an intake manifold and an exposure manifold, said fifteen volumes corresponding to fifteen air exchanges. In another method embodiment, starting and stopping a flow through the manifold until the at least one of the retrospective and the prospective inhaled dose is greater than or equal to a specified dose is characterized by: starting the flow of inhalant through the manifold in response to specification of at least one of an upper concentration limit, a lower concentration limit, a volume of an intake manifold, a volume of an exposure manifold, a respiratory minute volume of an animal in an animal port, a waste product concentration, and a dose to be delivered to the animal in the animal port. In another method embodiment, said starting and stopping a flow through the manifold until the at least one of the retrospective and the prospective inhaled dose is greater than or equal to a specified dose is characterized by: activating at least one of an input flow and an exhaust flow such that a desired flow rate is achieved. In another method embodiment, starting and stopping a flow through the manifold until the at least one of the retrospective and the prospective inhaled dose is greater than or equal to a specified dose is characterized by: activating at least one of an input flow and an exhaust flow such that a desired chamber pressure is achieved. In another method embodiment, starting and stopping a flow through the manifold until the at least one of the retrospective and the prospective inhaled dose is greater than or equal to a specified dose is characterized by: reducing an input flow down to substantially only that necessary to operate an inhalant characterization device. In another method embodiment, starting and stopping a flow through the manifold until the at least one of the retrospective and the prospective inhaled dose is greater than or equal to a specified dose is characterized by: substantially stopping an exhaust flow.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing—referenced method embodiments depending upon the design choices of the system designer.

In one embodiment, a system includes but is not limited to: at least one manifold; an inhalant dissemination device coupled to the at least one manifold; an inhalant characterization device coupled to the at least one manifold; and a control module operably coupled to the inhalant dissemination device and the inhalant characterization device, said control module configured to (1) determine an inhalant concentration in a manifold, (2) calculate at least one of a retrospective and a prospective inhaled dose in response to the inhalant concentration, and (3) start and stop a flow through the manifold until the at least one of the retrospective and the prospective inhaled dose is greater than or equal to a specified dose. In another system embodiment, the control module operably coupled to the inhalant dissemination device and the inhalant characterization device is characterized by: a program running on a computer system, said computer system operably coupled to at least one of the inhalant dissemination device and the inhalant characterization device. In another system embodiment, the control module operably coupled to the inhalant dissemination device and the inhalant characterization device is characterized by: an ASIC, said ASIC operably coupled to at least one of the inhalant dissemination device and the inhalant characterization device.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

FIG. 2 depicts a pictographic representation of exposure chamber 100.

DETAILED DESCRIPTION OF THE INVENTION

A. Introduction

Figure 1:
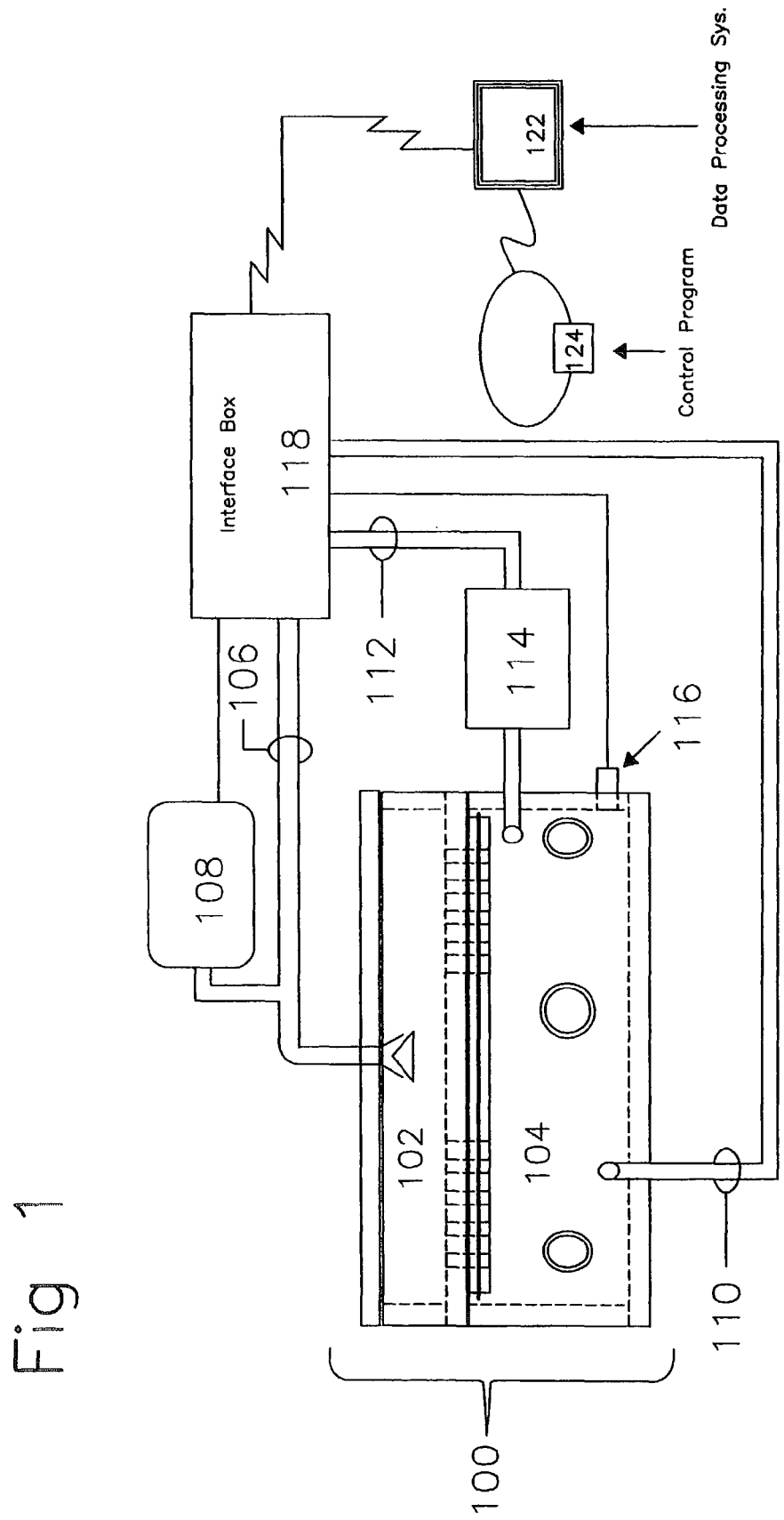
FIG. 1 shows a high level pictographic representation of an exposure system and associated hardware.

The subject matter described herein entails a method and associated system for generating a cycle of dynamic and static test atmospheres designed to be used for aerosol characterization or exposing animals to all materials potentially aerosolized, but especially limited production materials such as new chemical entities or biologics. In one application, the method and system will greatly reduce the cost and time required for evaluation of precious materials under testing. The method and system include complete computer automated control (see herein incorporated by reference in its entirety U.S. Pat. No. 6,904,912 B2) of aerosol generation, characterization, and exposure duration and can be utilized with a variety of commercially-available aerosol generators, sampling devices, and material types.

1. System Hardware

A high level pictographic representation of an exposure system and associated hardware is included as FIG. 1. Depicted is exposure chamber 100 composed of two distinct sections: intake manifold 102, and exposure manifold 104. Shown connected to intake manifold 102 is input air hose 106. Integral with input air hose 106 is inhalant dissemination device 108. Inhalant dissemination device 108 is meant to be indicative of a variety of different devices for dispersing organic or inorganic substances in an aerosol, gas, fume, dry powder, fiber or other suitable form. Connected to exposure manifold 104 is output air hose 110, and sampling air hose 112. Integral with sampling air hose 112 is inhalant characterization device 114. Inhalant characterization device 114 is meant to be indicative of a variety of different devices for characterizing the concentration of an inhalant in an aerosol, gas, fume, dry powder, fiber or other form. Environmental sensor 116 is also shown integral with exposure manifold 104 in FIG. 1. Environmental sensor 116 is meant to be indicative of a variety of sensors for characterizing the environmental conditions, including but not limited to temperature, relative humidity, and pressure, in exposure manifold 104: Also shown in FIG. 1 are input air hose 106, inhalant dissemination device 108, output air hose 110, sampling air hose 112, inhalant characterization device 114, and environmental sensor 116 all operably coupled with interface box 118. Interface box 118 houses the necessary power supplies, input airflow drivers, output airflow drivers, data acquisition hardware, and other associated electronics for the devices described herein. Further illustrated is interface box 118 operably coupled to data processing system 122. Residing in and running on data processing system 122 is specially developed control program 124 where such control program controls the various drivers, sensors, and other electronic devices in interface box 118 and associated with exposure chamber 100.

With reference now to FIG. 2, depicted is a pictographic representation of exposure chamber 100.Shown are elevation and plan view drawings of intake manifold 102, and exposure manifold 104. Intake manifold 102 includes input air coupler 202. Input air coupler 202 provides the mechanism for coupling input air hose 106 (not shown in FIG. 2) with intake manifold 102. Also shown is diffuser 204. Diffuser 204 provides the mechanism for distributing air entering intake manifold 102 via input air coupler 202 throughout intake manifold 102. Also shown in FIG. 2 are diffusion holes 206. Diffusion holes 206 provide the mechanism for the inhalant to pass out of intake manifold 102.

Further with reference to FIG. 2 is shown exposure manifold 104. Integral with exposure manifold 104 are animal ports 208.Animal ports 208 are meant to be indicative of one or several ports for allowing all or part of an animal or test subject to be exposed to the inhalant in exposure manifold 104. Also integral with exposure manifold 104 is output air coupler 210. Output air coupler 210 provides the mechanism for coupling output air hose 110 (not shown in FIG. 2) with exposure manifold 104.Further with reference to FIG. 2, shown is inhalant characterization device coupler 212. Inhalant characterization device coupler 212 provides the mechanism for coupling exposure chamber 104 with inhalant characterization device 114 (not shown in FIG. 2). Environmental sensor 116 is shown coupled to exposure manifold 104. Environmental sensor 116 is meant to be indicative of a variety of sensors for characterizing the environmental conditions, including but not limited to temperature, relative humidity, and pressure, in exposure manifold 104.

2. System Operation:

When utilizing the system the operator first loads animals into exposure ports 208 and the inhalant into inhalant dissemination device 108. On the graphical user interface (GUI) associated with control program 124 running on data processing system 122, the user enters upper and lower concentration limits for exposure manifold 104, the volume of intake manifold 102, the volume of exposure manifold 104, the respiratory minute volume of the subjects in animal ports 208, and the dose to be delivered to the subjects. In another embodiment, the respiratory minute volume of the subjects is actually measured utilizing techniques analogous to the above cited, and herein incorporated by reference in their entireties, United States patent applications. Via the GUI, the user then initiates the exposure.

Upon initiation, control program 124 begins an inhalant generation cycle. During the inhalant generation cycle, control program 124 in conjunction with interface box 118:

a. Disseminates the inhalant via inhalant dissemination device 108.
b. Generates any air flow through input air hose 106 required to operate dissemination device 108 or carry the inhalant into intake manifold 102.
c. Generates exhaust air flow through output air hose 110 as required to maintain the chamber pressure (as measured by environmental sensor 116) at the level defined by the user.
d. Generates any air flow through sampling air hose 112 required for operation of inhalant characterization device 114.
e. Monitors the inhalant concentration via inhalant characterization device 114.

Thereafter, control program 124 maintains the system in the inhalant generation cycle until the inhalant concentration, as measured by inhalant characterization device 114, exceeds the upper concentration limited defined by the user. When the inhalant concentration exceeds said limit, control program 124 initiates the static cycle.

During the static cycle control program 124 in conjunction with interface box 118:

a. Terminates operation of inhalant dissemination device 108, thereby stopping the generation of the inhalant.
b. Reduces the air flow through input air hose 106 to only that which may be required to balance the flow required to operate inhalant characterization device 114.
c. Stops the air flow through output air hose 110.
d. Maintains any air flow through sampling air hose 112 required for operation of inhalant characterization device 114.
e. Monitors the inhalant concentration via inhalant characterization device 114.

In one implementation, control program 124 maintains the system in the static cycle until the inhalant concentration as measured by inhalant characterization device 114 falls below the lower concentration limit defined by the user. When the inhalant concentration falls below said limit, control program 124 again initiates the inhalant generation cycle. These cycles continue until control program 124 indicates that the exposure is complete (the method by which control program makes this termination is described herein).

In one implementation, control program 124 initiates a chamber wash routine when the exposure is complete.

During the chamber wash routine, control program 124 in conjunction with interface box 118:

a. Terminates operation of inhalant dissemination device 108, thereby stopping the generation of the inhalant.
b. Generates an air flow through input air hose 106 at a rate equal to that used in the inhalant generation cycle previously described.
c. Generates an air flow through output air hose 110 sufficient to maintain the pressure in exposure manifold 104 (as measured by environmental sensor 116) at the level defined by the user.
d. Maintains any air flow through sampling air hose 112 required for operation of inhalant characterization device 114.
e. Monitors the inhalant concentration via inhalant characterization device 114.

In one implementation, control program 124 continues the wash routine until its timer function indicates that 15 complete air changes have occurred in intake manifold 102 and exposure manifold 104. After the 15 air changes are complete, control program 124 terminates all air flows, terminates inhalant concentration monitoring, notifies the user via the GUI that the exposure sequence is complete, and displays the measured delivered dose on the GUI. (The method for determining the measured delivered dose will be described.)

3. Description Of Dose Calculation Functions:

During the inhalant generation and static cycles, control program 124 makes at least two calculations in near real-time. First, control program 124 uses the inhalant concentration measurement from inhalant characterization device 114, the elapsed time, and the respiratory minute volume to relatively continuously calculate the dose delivered to the subjects (Delivered Dose Calculation). Second, control program 124 uses the inhalant concentration measurement from inhalant characterization device 114, the volumes of intake manifold 102 and exposure manifold 104, and the respiratory minute volume to continuously calculate the dose that would be delivered to the subjects during the chamber wash routine if it were initiated immediately (Projected Chamber Wash Dose Calculation). When control program 124 indicates that the sum of these two dose calculations (Delivered Dose Calculation plus Projected Chamber Wash Dose Calculation) is equal to the user-defined dose to be delivered to the subjects, control program 124 initiates the chamber wash routine. Consequently, when the chamber wash routine is completed, the test subjects will have received the desired dose. The foregoing is the method by which control program 124 determines when the exposure is complete and the chamber wash routine initiated.

a. Delivered Dose Calculation

Inhaled dose in an inhalation toxicology study is determined by the following equation:

$$Dose = \int_0^{t_{exp}} R(t) \times C(t) \, dt$$

where R(t) is the animal respiratory rate in units of volume per unit time, and C(t) is the chamber inhalant concentration in units of mass per unit volume, and $t_{exp}$ is the time duration of the exposure.

Several assumptions are often made to simplify this calculation. Typically, a steady state inhalant concentration, C(t), is assumed in the exposure chamber. Additionally, a constant rate of respiration, R(t), is assumed for the test animal. This constant respiratory rate is determined either by historical estimates based on the animal weight, or on actual respiratory function measurements taken prior to the exposure. If the inhalant concentration and animal respiratory function are assumed constant as described, the dose calculation integral reduces to a simple product:

$$Dose = R \times C \times t_{exp}$$

In the present invention, the inhalant concentration in the exposure chamber varies. Starting and stopping of the flow of the inhalant results in increasing and decreasing inhalant concentrations throughout the course of the exposure. Therefore, since the inhalant concentration is manifestly not a constant function of time, the methodology for dose calculation previously described cannot be applied.

In the present invention, inhalant concentration monitoring device 114 is employed to measure the inhalant concentration, C(t), as a function of time. Control program 124 uses these values in conjunction with the dose calculation integral to perform the Delivered Dose Calculation.

In one implementation, the animal respiratory function, R(t), is assumed to be constant. R is estimated using the animal weight and based on an empirically derived formula: $MV = 2.1 \ast W^{0.75}$ where MV is the respiratory minute volume in milliliters, and W is the animal mass in grams. In this implementation, the dose calculation integral simplifies to $$Dose = R \int_0^{t_{exp}} C(t)\,dt$$

since R is not a function of time. Control program 124 utilizes the inhalant concentration measurement as determined by inhalant characterization device 114 to continuously calculate the value of the integral component of this simplified dose equation. Control program 124 performs the Delivered Dose Calculation by multiplying this integral component by the constant term R, thus generating a running total of the inhaled dose.

In a second implementation, the methodology previously described (see U.S. patent application Ser. No 10/166,228 which is hereby incorporated by reference in its entirety) is employed to measure the animal respiratory function in near real time. In this implementation, both the inhalant concentration, C(t), and the animal respiratory function, R(t), are measured functions of time. To calculate the inhaled dose, the full dose calculation integral $$Dose = \int_0^{t_{exp}} R(t) \times C(t)\,dt$$

is utilized. Control program 124 utilizes the inhalant concentration measurement as determined by inhalant characterization device 114, as well as the respiratory function measurement made using the aforementioned method, to continuously perform the Delivered Dose Calculation. Using this methodology, control program 124 generates a running total of the inhaled dose of the inhalant.

b. Projected Chamber Wash Dose Calculation

Control program 124 continues to use the inhalant concentration measurement from inhalant characterization device 114 to make the Delivered Dose Calculation during the chamber wash routine in near real-time. When the chamber wash routine is complete, control program 124 displays the final Delivered Dose Calculation on the GUI as the measured delivered dose.

In one implementation, the Projected Chamber Wash Dose Calculation is calculated as follows.

i. Calculation Variables:

V Volume of exposure chamber (intake+exposure manifolds) [liters]

M(t) Mass of inhalant in exposure chamber at time t $Q_1$ Flow rate during inhalant generation cycle [liters/minute]

MV Total rate of animal respiration [liters/minute]

ii. Calculation Assumptions:

In one implementation, the calculation is based on the following assumptions.

(a) Uniform Manifold Concentration

In one implementation, it is assumed that the concentration of the inhalant is uniform throughout both the intake and exposure manifolds. In equation form, this assumption may be expressed as follows:

$$\nabla M(x,y,z) = 0$$

(b) Rate of Loss of Inhalant

In one implementation, it is assumed that for any mechanism by which the inhalant leaves the inhalation system (including inhalation by the animals, through the exhaust flow, settling, etc.), the rate of loss of the inhalant is directly proportional to the inhalant concentration in the inhalation system. In equation form, this assumption may be expressed as follows:

$$\frac{\partial M(t)}{\partial t} \alpha M(t)$$

In one implementation, this can be seen as follows. At the start of the chamber wash cycle, there is no aerosol generation. Input and exhaust flows are equal to $Q_1$. The mass in the chamber as a function of time behaves as:

$$\frac{\partial M(t)}{\partial t} = -\frac{Q_1}{V} M(t) - \frac{MV}{V} M(t)$$

If $M(0) = M_0$, solving this differential equation results in an expression for mass of inhalant in the chamber as a function of time:

$$M(t) = M_0 e^{-\frac{(Q_1 + MV)}{V} t}$$

Dividing both sides by the chamber volume (V) yields an expression for the chamber concentration, C(t), during an air wash as a function of time:

$$C(t) = C_0 e^{-\frac{(Q_1 + MV)}{V} t}$$

iii. Projected Dose Delivered During Wash Cycle

If the wash duration lasts a duration such that 15 complete air exchanges occur in the chamber, then the total dose delivered can be calculated:

$$D_{Total} = \int_0^{\frac{15V}{Q_1}} MV \times C(t)\,dt$$

Substituting the expression for C(t):

$$D_{Total} = \int_0^{\frac{15V}{Q_1}} MV \times C_0 e^{\frac{-(Q_1+MV)}{V}t}\,dt$$

$$D_{Total} = MV \times C_0 \int_0^{\frac{15V}{Q_1}} e^{\frac{-(Q_1+MV)}{V}t}\,dt$$

$$D_{Total} = MV \times C_0 \left(\frac{-V}{Q_1+MV}\right) e^{\frac{-(Q_1+MV)}{V}t}\Big|_{t=0}^{t=\frac{15V}{Q_1}}$$

$$D_{Total} = MV \times C_0 \left(\frac{-V}{Q_1+MV}\right)\left(e^{\frac{-(Q_1+MV)}{V}\frac{15V}{Q_1}} - 1\right)$$

$$D_{Total} = \frac{MV \times C_0 \times V}{Q_1+MV}\left(1 - e^{-15\left(1+\frac{V \times MV}{Q_1}\right)}\right)$$

Since $\text{Exp}(-15) < 10^{-6}$, the exponential term can be assumed to be 0.

Consequent, in one implementation the total dose delivered during a wash cycle then equals:

$$D_{Total} = \frac{MV \times C_0 \times V}{Q_1+MV}$$

iv. Wash Cycle Initiation

Using the foregoing equations, the computer algorithm can calculate the projected chamber wash dose. The Minute Volume [MV], Chamber Volume [V], and Inhalant Generation Cycle Flow ($Q_1$) are all entered by the user. The Chamber Concentration ($C_0$) is determined by the chamber concentration monitor.

Thus, the algorithm continuously calculates, using the above equation and the measurement from the concentration monitor, the dose that would be delivered if the wash cycle were immediately initiated (i.e. the current concentration reading would become $C_0$ in the above equation). When that value plus the dose already delivered equals the total dose to be delivered during the aerosol, the algorithm initiates the chamber wash cycle. In this way, the dose can be accurately delivered, taking into account the dose that will be delivered as the aerosol is evacuated from the exposure chamber.

Control program 124 continues to use the inhalant concentration measurement from inhalant characterization device 114 to make the Delivered Dose Calculation during the chamber wash routine in near real-time. When the chamber wash routine is complete, control program 124 displays the final Delivered Dose Calculation on the GUI as the measured delivered dose.

4. Non-Exhaustive Examples of Advantages of Subject Matter Disclosed Herein over Other Devices, Systems or Processes The subject matter disclosed herein offers a number of advantages over other inhalant systems. For example, the subject matter provides a platform exploiting the advantages of both dynamic and static inhalant systems while, overcoming many drawbacks of each. A few specific advantages are set forth following; those having ordinary skill in the art will recognize that such advantages constitute a non-exhaustive listing.

a. Some Advantages over Dynamic Inhalant Systems

In some implementations, the subject matter disclosed herein achieves aerosol efficiencies that far exceed those which can be attained using dynamic inhalant systems. Dynamic inhalant systems generally operate by supplying and exhausting the inhalant from the exposure chamber at a constant rate. This process results in most of the inhalant being exhausted from the chamber and not inhaled by the test subject. The efficiency of such systems is typically about 1% (although those skilled in the art will recognize that some specialized systems have efficiencies up to 10%), where efficiency is defined as the mass of inhalant inhaled by the test animal divided by that used in generating the inhalant environment. In one implementation, the subject matter disclosed herein utilizes a dynamic cycle to achieve a user defined upper inhalant concentration, and then a static cycle to maximize the amount of inhalant inhaled by the test animal. Use of the static cycle minimizes the amount of inhalant exhausted from the chamber and results in system efficiencies as high as 40%. This improved efficiency significantly reduces the quantity of inhalant that must be produced to conduct inhalation toxicology studies. Furthermore, it should be noted that irrespective of the base efficiencies of dynamic systems, the subject matter disclosed herein can be used to improve the efficiencies of such dynamic systems beyond their base efficiencies.

In some implementations, the subject matter disclosed herein includes a method to study "aged" aerosols. In many inhalation studies the material under testing must have a long residence time in the inhalant phase to achieve the conditions needed for effective testing. In dynamic inhalant systems, the inhalant residence time in the chamber is on the order of one second. The subject matter disclosed herein utilizes a dynamic cycle to generate the inhalant environment, and then a static cycle to maximize the residence time of the inhalant in the inhalation chamber. Use of the static cycle allows residence times of the inhalant in the chamber of many minutes. These longer residence times allow studies of "aged" aerosols that heretofore could not be conducted in dynamic inhalant systems.

b. Some Advantages over Static Inhalant Systems

In some implementations, the subject matter disclosed herein includes a method for near real-time dose calculation. In static inhalation systems, the cycle times must be determined prior to the exposure, and the dose must be calculated after the exposure is complete. The subject matter disclosed herein utilizes near real-time inhalant concentration monitoring in conjunction with the control program to calculate the inhaled dose in near real-time.

In some implementations, the subject matter disclosed herein allows for delivery of virtually any inhalant dose to the test subjects with virtually any starting concentration of the material under testing. Static inhalant systems require that the dose be delivered to the test subjects in discrete static dose units. In one implementation, the dose calculation function included in the subject matter disclosed herein generates a running total of dose delivered. The control program initiates the exposure termination sequence when the existing dose plus that to be delivered during the termination sequence equals the dose entered by the user. This implementation allows virtually any dose to be delivered to virtually any group of test subjects with any virtually starting concentration, thus overcoming the drawback of other static inhalant systems that doses be delivered in discrete units.

In some implementations, the subject matter disclosed herein provides for automatic control of the inhalant concentration in the inhalant chamber. Generally, other static inhalant systems require the user to repeatedly initiate and terminate inhalant dissemination manually and do not incorporate a method for continuously and automatically maintaining the inhalant concentration at user-defined levels. In one implementation, the inhalant generation and static cycle innovations described previously provide for automatically and continuously controlling the inhalant concentration in a static inhalant system.

In some implementations, the subject matter disclosed herein provides for automatically accounting for changes in the number or respiratory minute volumes of the test animals. Generally, static inhalant systems require complete system recharacterization if the number or respiratory minute volumes of animals in the system changes. Generally, static inhalant systems rely on pre-determined cycle times that are a function of the number and respiratory minute volumes of the test animals. In one implementation, the subject matter disclosed herein varies the inhalant generation and static cycle times based on near real-time inhalant concentration measurements rather than on predetermined cycle durations. This feature, in conjunction with the near real-time dose calculation function, eliminates the need to recharacterize the subject matter disclosed herein when changing the number or species of the test subjects.

In some implementations, the subject matter disclosed herein provides for the exhausting of carbon dioxide, ammonia, and other animal byproducts from the inhalant chamber. Generally, static inhalation systems generate environments rich in carbon dioxide and ammonia near the end of each exposure cycle. Such systems do not provide processes or methods for automatically exhausting and regenerating the inhalant environment when carbon dioxide loading becomes too severe. In one implementation, the inhalant concentration control innovation in the subject matter disclosed herein provides a process by which the user can ensure that carbon dioxide loading is limited. The near real-time inhalant concentration measurement provides an indirect measure of carbon dioxide loading. Each animal breath results in inhalant being removed from the inhalant chamber and carbon dioxide being added. Thus, carbon dioxide concentration varies inversely with inhalant concentration. The user, therefore, indirectly limits carbon dioxide loading by choosing an appropriate inhalant concentration lower limit.

In another implementation, the carbon-dioxide concentration is measured directly with a sensor, and the environment is controlled in response thereto. In yet another implementation, the ammonia concentration is measured directly with a sensor, and the environment is controlled in response thereto.

5. Non-Exhaustive List of a Few of the Differences between the Subject Matter Disclosed Herein and Other Systems A listing of a few of the differences between the subject matter disclosed herein and other methods and systems follow. Those having ordinary skill in the art will recognize that such differences constitute a non-exhaustive listing.

One difference between the subject matter disclosed herein and other methods and systems is that in one implementation the subject matter disclosed herein generates a preferred exposure atmosphere by cycling between a dynamic and static state.

Another difference between the subject matter disclosed herein and other methods and systems is that in one implementation of the subject matter disclosed herein the atmosphere in an exposure chamber is controlled to achiever a desired inhaled dose in an animal housed in the exposure chamber without reliance on a continuous atmospheric concentration.

Another difference between the subject matter disclosed herein and other methods and systems is that in one implementation of the subject matter disclosed herein a presented dose to an animal is determined based on the individual respiration of the animal and the constantly fluctuating exposure concentrations using both dynamic and static states.

Another difference between the subject matter disclosed herein and other methods and systems is that in one implementation of the subject matter disclosed herein a preferred inhaled dose is delivered to a test subject in a static exposure chamber regardless of the concentration of the starting material in the aerosol generator.

Another difference between the subject matter disclosed herein and other methods and systems is that in one implementation of the subject matter disclosed herein a preferred inhaled dose is delivered to a test subject in a static chamber regardless of the respiratory minute volume of said subject.

Another difference between the subject matter disclosed herein and other methods and systems is that in one implementation of the subject matter disclosed herein automated, user-defined, concentration-based removal of gaseous animal byproducts from a static exposure chamber is provided.

Another difference between the subject matter disclosed herein and other methods and systems is that in one implementation of the subject matter disclosed herein the quantity of material under testing required to deliver a desired dose to a test animal is reduced.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method comprising:

starting a flow of an inhalant having at least one non-ambient constituent through an exposure manifold;

determining an inhalant concentration of the inhalant in the exposure manifold;

stopping the flow of the inhalant through the exposure manifold when the inhalant concentration is in a first specified inhalant-concentration range;

determining a metabolic waste product concentration in the exposure manifold; and repeating said starting, determining, and stopping when the metabolic waste product concentration is in a first specified range.

2. The method of claim 1, wherein the first specified inhalant-concentration range comprises:

an inhalant concentration greater than or equal to a specified threshold concentration.

3. The method of claim 1, wherein said repeating occurs when the inhalant concentration is in a second specified inhalant-concentration range, the second specified inhalant-concentration range comprises:

an inhalant concentration less than or equal to a specified threshold concentration.

4. The method of claim 1, wherein the metabolic waste product concentration comprises:

a biological waste product concentration greater than or equal to a specified threshold concentration.

5. The method of claim 1, wherein the metabolic waste product comprises:

at least one metabolic waste product of the metabolic-waste product group including but not limited to carbon dioxide and ammonia.

6. The method of claim 1, wherein
stopping the flow of the inhalant through the exposure chamber when the inhalant concentration is in a first specified inhalant-concentration range includes reducing an input air flow down to substantially only that necessary to operate an inhalant characterization device.

7. The method of claim 6, wherein said stopping the flow of the inhalant through the exposure chamber when the inhalant concentration is in a first specified inhalant-concentration range comprises:
substantially stopping an exhaust flow.

8. The method of claim 1, wherein said stopping the flow of the inhalant through the exposure manifold when the inhalant concentration is in a first specified inhalant-concentration range comprises:
substantially stopping an exhaust flow.

9. The method of claim 1, wherein stopping the flow of the inhalant includes substantially stopping an air flow into the exposure chamber.

10. The method of claim 9, wherein substantially stopping the air flow includes allowing sufficient air flow to allow for measurement of the inhalant concentration.

11. The method of claim 1, wherein stopping the flow of the inhalant includes substantially stopping an air flow into and out of the exposure chamber.

12. The method according to claim 1, further comprising inserting a plurality of animals through animal ports in the exposure manifold such that the animals are exposed to the inhalant in the exposure manifold.

13. The method of claim 1, wherein the flow of inhalant passes through the exposure chamber into an exhaust.

14. The method of claim 1, further comprising removing the plurality of animals from the exposure chamber after completion of the exposure, and
wherein at least one repeating occurs prior to removal of the plurality of animals.

15. A computer-readable medium having computer-executable instructions for performing the method steps recited in claim 1.

16. A system comprising:
means for starting a flow of an inhalant having at least one non-ambient constituent through an exposure manifold;
means for determining an inhalant concentration of the inhalant in the exposure manifold;
means for stopping the flow of the inhalant through the exposure manifold when the inhalant concentration is in a first specified inhalant-concentration range;
means for determining a metabolic waste product concentration in the exposure manifold;
means for operating said starting means, said determining means, and said stopping means when the metabolic waste product concentration is in a first specified range.

17. The system of claim 16, wherein the metabolic waste product concentration comprises:
a biological waste product concentration greater than or equal to a specified threshold concentration.

18. The system of claim 16, wherein the metabolic waste product comprises:
at least one metabolic waste product of the metabolic-waste product group including but not limited to carbon dioxide and ammonia.

19. The system of claim 16, wherein said means for stopping the flow of the inhalant through the exposure manifold when the inhalant concentration is in a first specified inhalant-concentration range comprises:
means for reducing an input flow down to substantially only that necessary to operate an inhalant characterization device.

20. The system of claim 16, wherein said means for stopping the flow of the inhalant through the exposure manifold when the inhalant concentration is in a first specified inhalant-concentration range comprises:
means for substantially stopping an exhaust flow.

21. The system according to claim 16, further comprising means for exposing a plurality of animals.

22. The system of claim 16, further comprising an exhaust connected to said exposure chamber.

23. A method comprising:
exposing at least one animal to the atmosphere contained within an exposure chamber;
starting a flow of an inhalant having at least one non-ambient constituent into the exposure chamber;
exhausting the exposure chamber;
measuring an inhalant concentration of the inhalant in the exposure chamber;
stopping the flow of the inhalant and exhausting of the exposure chamber when the inhalant concentration is above an upper concentration limit;
repeating said starting, exhausting, and stopping when the inhalant concentration is below a lower concentration limit;
determining a metabolic waste product concentration in the exposure chamber; and
repeating said starting, exhausting, and stopping when the metabolic waste product concentration is above a predetermined metabolic waste product threshold; and
wherein a static inhalation study occurs once the inhalant concentration has exceeded the upper concentration limit and until at least one of the inhalant concentration is below the lower concentration limit, metabolic waste product threshold is exceeded, or an exposure level has been determined to have been reached or will be reached once the exposure chamber is flushed; and other times a dynamic inhalation study occurs.

* * * * *